United States Patent

Konoike et al.

[11] Patent Number: 5,354,879
[45] Date of Patent: Oct. 11, 1994

[54] OPTICALLY ACTIVE INTERMEDIATE AND METHOD FOR PRODUCTION THEREOF

[75] Inventors: Toshiro Konoike, Suita; Yoshitaka Araki, Amagasaki, both of Japan

[73] Assignee: Shionogi Seiyaku Kabushiki Kaisha, Osaka, Japan

[21] Appl. No.: 969,249

[22] PCT Filed: May 14, 1992

[86] PCT No.: PCT/JP92/00611

§ 371 Date: Feb. 19, 1993

§ 102(e) Date: Feb. 19, 1993

[87] PCT Pub. No.: WO92/22560

PCT Pub. Date: Dec. 23, 1992

[30] Foreign Application Priority Data

Jun. 19, 1991 [JP] Japan .................... 3-176209

[51] Int. Cl.$^5$ .................... C07F 7/08; C07F 7/18
[52] U.S. Cl. .................... 556/405; 556/428; 556/429; 556/437; 549/214; 558/44; 558/45; 558/52; 560/179; 560/187; 562/581; 562/583
[58] Field of Search ............... 556/405, 428, 429, 437; 549/214; 558/44, 45, 52; 560/179, 187, 266; 562/581, 583

[56] References Cited

U.S. PATENT DOCUMENTS 3,907,852  9/1975  Oswald et al. .................... 556/405

FOREIGN PATENT DOCUMENTS 0340007  2/1989  European Pat. Off. .
0414206  2/1991  European Pat. Off. .
49-18852  2/1974  Japan .
64-45337  2/1989  Japan .
1-132547  5/1989  Japan .
2-243650  9/1990  Japan .
2-250852  10/1990  Japan .

*Primary Examiner*—Paul F. Shaver
*Attorney, Agent, or Firm*—Morrison & Foerster

[57] ABSTRACT

The present invention relates to a synthetic method of optically active starting materials for various medicaments, which are represented by Formula (I):

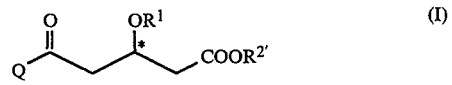

wherein $R^1$ is hydrogen or hydroxy protecting group; * is an asymmetric carbon; $R^{2'}$ is hydrogen or an optionally substituted lower alkyl; and Q is $-CH=P(Ph)_3$, $-CH_2P(O)(OMe)_2$, or $-CH_2S(O)Me$, in high optical purity on a large scale.

In more detail, the present invention provides intermediates and a method for the production thereof for synthesizing optically active compounds which are able to inhibit activities of HMG-CoA reductase and are, therefore, useful for inhibition of cholesterol biosynthesis.

6 Claims, No Drawings

OPTICALLY ACTIVE INTERMEDIATE AND METHOD FOR PRODUCTION THEREOF

FIELD OF THE INVENTION

The present invention provides optically active compounds useful as starting materials for various medicaments and a method for production thereof. For example, in a large scale production of optically active HMG-CoA reductase inhibitors in a high yield, optically active carboxylic esters provided by the present invention are very important.

BACKGROUND ART

It is generally known that the above-mentioned type of optically active compounds are obtainable through optical resolution of racemate or an asymmetric synthetic route. Conventional routes require, however, some special reagents or enzymes, or sometimes cumbersome steps. Furthermore, only a few methods for optical resolution of this type of compounds can give high optical purity enough for practical use.

Therefore, obtaining compounds of high optical purity is extremely important for synthesizing various compounds e.g., medicaments.

DISCLOSURE OF THE INVENTION

The present invention provides a simple asymmetric synthetic route for compounds of high optical purity on a large scale which utilizes a stereoselective reaction employing inexpensive reagents.

Under the circumstances described above, after a great many research efforts, the present inventors have found a method for production of optically active compounds useful as intermediates.

Namely, the present invention provides a method for production of compounds of high optical purity which are represented by Formula I:

$$Q \underset{O}{\overset{\|}{\diagup}} \underset{*}{\overset{OR^1}{\diagup}} COOR^{2'} \qquad (I)$$

(wherein
  $R^1$ is hydrogen or a hydroxy protecting group;
  $R^{2'}$ is hydrogen or optionally substituted lower alkyl;
  Q is —CH=P($R^3$)$_3$ or —CHX'X
  wherein
    $R^3$ is optionally substituted lower alkyl or optionally substituted aryl;
    X is —P(O)$R^4R^5$ or —S(O)$R^4$
    wherein
      $R^4$ and $R^5$ each is hydrogen optionally substituted lower alkyl, optionally substituted lower alkoxy, optionally substituted aryl, or halogen;
    X' is hydrogen or lower alkyl;
  * is an asymmetric carbon).

Namely, the present method for production comprises converting a compound (II-(R)) or (II-(S)):

$$HO \underset{O}{\overset{\|}{\diagup}} \underset{\blacktriangledown}{\overset{OR^1}{\diagup}} COO\underset{\text{\tiny{''''}}}{\diagdown} \underset{COOH}{\overset{Ph}{\diagup}} \qquad \text{II-(R)}$$

(wherein $R^1$ is the same as defined above), or $$HO \underset{O}{\overset{\|}{\diagup}} \underset{\vdots}{\overset{OR^1}{\diagup}} COO\underset{\text{\tiny{''''}}}{\diagdown} \underset{COOH}{\overset{Ph}{\diagup}} \qquad \text{II-(S)}$$

(wherein $R^1$ is the same as defined above), to a target compound of optically active carboxylate (I) by the following method (a) or (b).

Method (a)

(1) The compound (II-(R)) or (II-(S)) is subjected to a transesterification, namely, the compound is reacted with an optionally substituted alcohol such as methanol, ethanol, or the like, in the presence of a base catalyst such as sodium alkoxide, pyridine, or aluminum alkoxide, to give a compound (III-(R)) or (III-(S)):

$$HO \underset{O}{\overset{\|}{\diagup}} \underset{\blacktriangledown}{\overset{OR^1}{\diagup}} COOR^2 \qquad \text{III-(R)}$$

(wherein $R^1$ is the same as defined above and $R^2$ is optionally substituted lower alkyl), or $$HO \underset{O}{\overset{\|}{\diagup}} \underset{\vdots}{\overset{OR^1}{\diagup}} COOR^2 \qquad \text{III-(S)}$$

(wherein $R^1$ and $R^2$ each is the same as defined above).

(2) Next, the free carboxylic acid is converted to acyl halide by a treatment with a halogenating agent (for example, phosphorus halide such as phosphorus trihalide, phosphorus pentahalide and the like, or thionyl halide), preferably in the presence of a basic material (e.g. an organic base such as pyridine), or converted to a mixed anhydride by treatment with haloformate (e.g. methyl chloroformate, ethyl chloroformate, iso-butyl chloroformate and the like) in the presence of a basic material (e.g. triethylamine and the like).

(3) Next, subjecting resultant to a reaction with phosphorus ylide:

$$(R^3)_3P=C\underset{R^5}{\overset{R^4}{\diagup}} \qquad \text{(IVa)}$$

(wherein $R^3$ $R^4$ and $R^5$ are respectively the same as defined above) and
if necessary, followed by a hydrolysis reaction, to give the target compound (Ia-(R)) or (Ia-(S)):

$$(R^3)_3P= \underset{O}{\overset{\|}{\diagup}} \underset{\blacktriangledown}{\overset{OR^1}{\diagup}} COOR^{2'} \qquad \text{Ia-(R)}$$

(wherein $R^1$, $R^{2'}$ and $R^3$ are respectively the same as defined above), or $$(R^3)_3P= \underset{O}{\overset{\|}{\diagup}} \underset{\vdots}{\overset{OR^1}{\diagup}} COOR^{2'} \qquad \text{Ia-(S)}$$

(wherein $R^1$, $R^{2'}$ and $R^3$ are respectively the same as defined above).

Method (b)

The compound (II-(R)) or (II-(S)) is reacted with CH₂X'X (IVb):
(wherein X and X' are respectively the same as defined above) in the presence of a base in an organic solvent, and further, if necessary, followed by esterification, to give respectively the target compound (Ib-(S)) or (Ib-(R)):

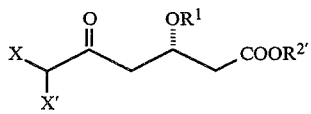

(wherein $R^1$ $R^{2'}$, X, and X' each is the same as defined above), or

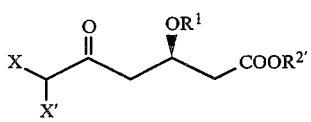

(wherein $R^1$ $R^{2'}$, X, and X' are respectively the same as defined above).

Namely, in method (a), the compound (Ia-(R)) is produced from (3R, 2'R) glutarate (II-(R)), and the compound (Ia-(S)) is produced from (3S, 2'S) glutarate (II-(S)). On the other hand, in the method (b), the compound (Ib-(S)) is produced from (II-(R)), and (Ib-(R)) is produced from (II-(S)).

Although both (R) and (S) forms of the compound (I) obtained in the above methods are useful, the (R) form is preferable as an intermediate of a HMG-CoA reductase inhibitor. Accordingly, the compound (Ia-(R)) produced from (3R, 2'R) glutarate (II-(R)) in the method (a), and the compound (Ib-(R)) produced from (3S, 2'S) glutarate (II-(S)) in the method (b) are used as more useful intermediates.

Furthermore, the compound (II) used as a starting material in the present invention is synthesized according to a method disclosed in the specification of Japanese Laid-Open Patent Publication No. 2-250852. Namely, an acid anhydride of the Formula:

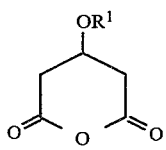

(wherein $R^1$ is the same as defined above) is reacted with (R)- or (S)-arylacetic acid derivatives in the presence of an alkyllithium reagent such as n-BuLi or the like, or a base such as sodium metal and the like, in an inert organic solvent (e.g. hexane, acetone, methylene chloride, benzene, toluene, dimethylformamide, or acetonitrile), to give (3R, 2'R) glutarate represented by Formula (II-(R)):

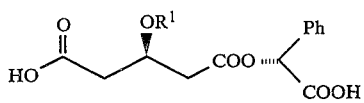

(wherein $R^1$ is the same as defined above) or to give (3S, 2'S) glutarate represented by Formula (II-(S)):

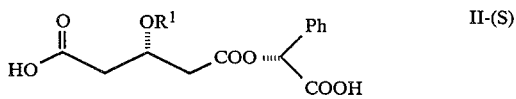

(wherein $R^1$ is the same as defined above).

In the present specification, the hydroxy protecting group means ether-forming protecting group such as methyl, tert-butyl, allyl, benzyl, tetrahydropyranyl, tert-butyldimethylsilyl, tert-butyldiphenylsilyl, and the like; ester-forming protecting group such as acetyl, benzoyl and the like; or sulfonate-forming protecting group such as methylsulfonyl, p-toluensulfonyl, phenylsulfonyl and the like, etc. Preferred in the invention is an ether-forming protecting group, especially tert-butyldimethylsilyl.

As used herein, the "optionally substituted lower alkyl" generally means straight or branched $C_1$-$C_6$alkyl such as methyl, ethyl, n-propyl, isopropyl, n-butyl, isobutyl, sec-butyl, tert-butyl, n-pentyl, isopentyl, neopentyl, tert-pentyl, 2-methylbutyl, n-hexyl, and isohexyl, or the like, all of which can be substituted by halogen, amino, and the like.

As used herein, the "optionally substituted lower alkoxy" means straight or branched $C_1$-$C_6$ alkyloxy, wherein the alkyl includes all the examples of the lower alkyl defined above.

As used herein, the "optionally substituted aryl" generally means $C_6$-$C_{12}$ aromatic group such as phenyl, tolyl, xylyl, biphenyl, naphtyl, and the like, and the aryl may be substituted with the above defined alkyl, alkoxy, halogen, or amino and the like. As used herein, halogen means fluorine, chlorine, bromine, iodine.

THE BEST MODE FOR CARRYING OUT THE INVENTION

The present invention is here after described in more detail by the following Examples, which are not intended to limit the scope of the present invention.

Each abbreviation in the Examples is defined as follows:

Me: methyl, Et: ethyl, Pr: propyl, Bu: butyl, Ph: phenyl.

EXAMPLE

Example 1

Methyl (3R) 3-(tert-butyldimethylsilyloxy)-5-oxo-6-triphenylphosphoranylidene hexanoate (Ia-(R)-1)

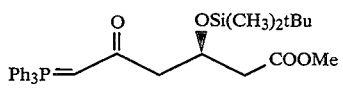

(Step 1)

Synthesis of the compound (III-(R)-1)

A solution of (3R) 3-[(tert-butyldimethylsilyl)oxy]-glutaric acid 1-((R)-(−)-mandelate)*¹ (65 g, 164 mmol)

in minimum volume, i.e., 60 ml of methanol is added dropwise to 28% sodium methoxide solution in methanol (310 ml, 1.6 mol) under nitrogen atmosphere at 0° C. over a period of 45 minutes, during which the internal temperature is kept equal or below 7° C. The reaction mixture is stirred at 0° C. for 30 minutes and then poured with stirring into a mixture of concentrated HCl (150 ml), water (300 ml), and methylene chloride (500 ml) under ice-cooling. The organic layer is separated and the aqueous layer is extracted with 200 ml of methylene chloride. Each organic layer is washed with diluted HCl and saturated brine successively, and then combined, dried over anhydrous magnesium sulfate and evaporated to give a half ester (III-(R)-1) (45.07 g, 163 mmol) in a 99% yield.

*1: This compound can be synthesized according to a method described in Japanese Laid-Open Patent Publication No. 2-250852, page 10.

$^1$HNMR (CDCl$_3$) δ:0.08 (s, 3H); 0.09 (s, 3H); 0.86 (s, 9H ); 2.52–2.73 (m, 4H ); 3.08 (s, 3H ); 4.55 (quintet, 1H, J=6 Hz) IR (CHCl$_3$): 2880, 1734, 1712, 1438, 1305, 1096, 836 cm$^{-1}$ [α]$_D$=−5.0±0.4° (C=1.04, 23.5° C., CHCl$_3$) Rf 0.32 (CHCl$_3$/MeOH=9/1)

(Step 2)

To a solution of the resulting compound (III-(R)-I) (553 mg, 2 mmol) in 10 ml of an ether are added dropwise triethylamine (0.362 ml, 2.6 mmol) and then ethyl chlorocarbonate (0.230 ml, 2.4 mmol) at −78° C. under nitrogen atmosphere. The reaction mixture is stirred for an additional 1 hour, washed with water and aqueous sodium carbonate, and dried over anhydrous sodium sulfate. From the resulting solution, the isopropyl ether is evaporated under vacuum to give 1,5-ethoxycarbonyl methyl-3-tert-butyl-dimethylsilyloxypentanedioate.

$^1$HNMR (CDCl$_3$) δ: 0.08 (3H, s); 0.09 (3H, s); 0.85 (9H, s); 1.3–1.4 (3H, t, J=7.3 Hz); 2.5–2.6 (2H, d, J=6.3 Hz); 2.6–2.8 (2H, m); 3.69 (3H, s); 4.26–4.38 (2H, q, J=7.3 Hz); 4.5–4.62 (1H, m)

Next, 60% sodium hydride and 1.29 g (3.6 mmol) of methyltriphenylphosphonium bromide are added to 20 ml of DMSO under nitrogen atmosphere, and stirred at 50° C. for 3 hours. To a solution of 1,5-ethoxycarbonyl methyl-3-tert-butyldimethylsilyloxypentanedioate in 10 ml of THF is added dropwise a solution of the methylene triphenylphosphorane obtained above in DMSO at −10° C. The reaction mixture is stirred for 1 hour and poured into water, and extracted with isopropyl ether. The extracted solution is dried over anhydrous sodium sulfate, concentrated; and then subjected to silica gel column chromatography (ethyl acetate) to give 740 mg of a target compound (Ia-(R)-1) in a 69% yield, which can be recrystallized from ether-hexane.

$^1$HNMR (CDCl$_3$) δ: 0.04 (s, 3H); 0.06 (s, 3H); 0.83 (s, 9H); 2.4–2.9 (m, 4H); 3.64 (s, 3H); 3.74 (d, 1H, $^2J_{PH}$=26 Hz); 4.5–4.7 (m, 1H); 7.4–7.8 (m, 15H) IR (CHCl$_3$): 2880, 1730, 1528, 1437, 1250, 1106, 835 cm$^{-1}$ [α]$_D$=−6.2° (C=1.27, 22.0° C., CHCl$_3$), mp.: 77.5°–78.5° C. Rf=0.48 (CHCl$_3$/MeOH=9/1) Analysis (%) for C$_{31}$H$_{39}$O$_4$PSi Calcd.: C,69.63; H,7.35; P,5.79 Found: C,69.35; H,7.35; P,6.09

Example 2(a)

Methyl (3R) 3-(tert-butyldimethylsilyloxy)-6-dimethoxyphosphinyl-5-oxohexanoate (Ib-(R)-1)

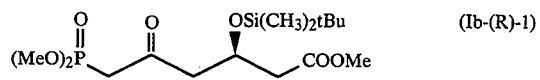

(1) To a solution of 2.44 ml (22.5 mmol) of dimethyl methylphosphonate in 30 ml of THF is added dropwise a solution of 14.1 ml of 1.6M n-butyllithium (22.5 mmol) in hexane at −78° C. under nitrogen atmosphere over 5 minutes. The reaction mixture is stirred at −78° C. for 30 minutes to give a white precipitate. To the resulting suspension is added dropwise a solution of 1.983 g (5 mmol) of (3S) 3-[(tert-butyldimethylsilyl) oxy]-glutaric acid 1-((S)-(+)-mandelate)*2 in 10 ml of THF over 5 minutes. The resulting slurry is stirred at −78° C. for 3 hours to give a homogeneous solution, which is extracted with an ice-cooled mixture of methylene chloride and 2N HCl. The methylene chloride layer is washed with water twice, dried over anhydrous magnesium sulfate, and condensing the solution to give crude carboxylic acid of ketophosphonate.

*2: This compound is synthesized from (s)-(+)-benzyl mandelate by the same method as that for (3R) 3-[(tertbutyldimethylsilyl)oxy]-glutaric acid 1-((R)-(−)-mandelate).

(2) Next, to a solution of the obtained extracted residue in 100 ml of ether is added dropwise an ether solution of diazomethane bit by bit under ice-cooling, until the evolution of nitrogen gas stops and the yellow color of the excess diazomethane persists. The solution is condensed and the oily residue is subjected to silica gel column chromatography (ethyl acetate) for purification, to give 831 mg of the target compound (Ib-(R)-1) with 43% yield. Rf=0.50 (ethyl acetate)

$^1$HNMR (CDCl$_3$, 200 MHz ) δ: 0.06 ( s, 3H ); 0.07 (s, 3H); 0.84 (s, 9H); 2.4–2.6 (m, 2H); 2.88 (d, 2H, J=6.2 Hz); 3.11 (d, 2H, 2J$_{PH}$=22.6 Hz); 3.67 (s, 3H); 3.76 (s, 3H); 3.82 (s, 3H); 4.47 (quintet, 1H, J=6.0 Hz) IR (CHCl$_3$): 2950, 2850, 1729, 1256, 1036, 836 cm$^{-1}$ Analysis (%) for C$_{15}$H$_{31}$OPSi Calcd.: C,47.11; H,8.17; P,8.10 Found: C,47.05; H,7.88; P,7.86

Example 2(b)

Alternative synthetic method of methyl (3R) 3-(tert-butyldimethylsilyloxy)-6-dimethoxyphosphinyl-5-oxohexanate (Ib-(R)-1)

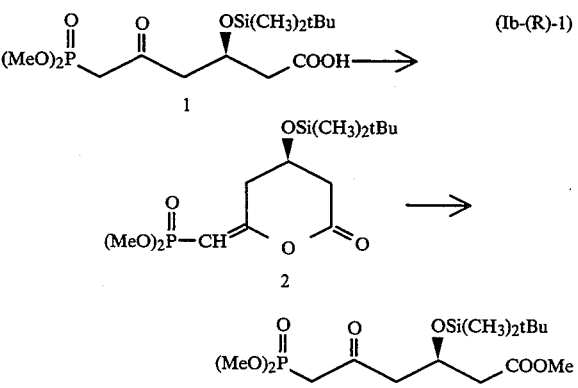

(1) To a solution of 841 mg (2.28 mM) of the compound 1 in 8.5 ml of methylene chloride is added 0.792 ml (5.7 mM) of triethylamine, and cooled to −78° C. and 0.212 ml (2.74 mM) of methanesulfonyl chloride is added thereto. The reaction mixture is gradually warmed up to room temperature and stirred for 30 minutes. The reaction mixture is poured into diluted HCl and extracted with methylene chloride. The extract is washed with aqueous sodium bicarbonate and dried over an anhydrous magnesium sulfate. The extract is concentrated to give 659 mg of the crude compound 2 (Z:E=1:3).

¹HNMR (CDCl₃) δ: 0.09 ( s, 6H ); 0.87 ( s, 9H ); 2.50–2.90 (m, 4H); 3.81 (d, 3H, J=11.2 Hz); 3.76 (d, 3H, J=11.2 Hz); 4.20–4.40 (m, 1H); 4.80–5.00 (m, 1H)

(2) To a solution of 659 mg of the compound 2 in 7 ml of methanol is added 0.18 ml of 1N sodium methoxide in methanol at 0° C., stirred at 0° C. for 20 minutes, poured into diluted HCl and extracted with methylene chloride. The extract is washed with aqueous solution of sodium bicarbonate, dried over anhydrous magnesium sulfate, concentrated, and subjected to column chromatography of silica gel, to give 481 mg of the compound (Ib-(R)-1) with a 67% yield.

Example 3(a)

Methyl (3R) 3-(tert-butyldimethylsilyloxy)-6-methylsulfinyl-5-oxohexanate (Ib-(R)-2)

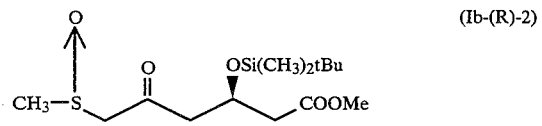

To a mixture of 270 ml of THF and 25.6 ml (0.36 mol) of dimethyl sulfoxide (DMSO) is added a solution of 1.6M of n-BuLi in n-hexane (168 ml) at −30° C., stirred for 20 minutes, then a solution of 23.79 g (60 mmol) of (3S) 3-[(tert-butyldimethylsilyl) oxy]-glutaric acid 1-((s)-(+)-mandelate in 120 ml of THF is added dropwise at −70° C. thereto. The reaction temperature is gradually raised up to −15° C., at which temperature it is stirred for 30 minutes, then poured into diluted HCl and extracted with methylene chloride. The organic layer is washed with diluted HCl and brine successively and dried over anhydrous magnesium sulfate, to give solution of crude carboxylic acid. Rf=0.8 (chloroform/methanol=3/1)

The solution of the obtained crude carboxylic acid is treated with diazomethane in ethyl ether added dropwise at −20° C, until the yellow color of diazomethane persists. The obtained solution of methyl ester is concentrated and then subjected to silica gel column chromatography (acetone/ethyl acetate=1/1) for purification, to give 14.43 g of the compound (Ib-(R)-2) in a 71% yield. Rf=0.3 (ethyl acetate)

¹HNMR (CDCl₃): 0.07 (3H, s); 0.09 (3H, s); 0.85 (9H, s); 2.5–2.6 (2H, m); 2.7 (3H, m); 2.8–3.0 (2H, m); 3.68 (3H, s); 3.7–3.9 (2H, m); 4.5–4.7 (1H, m)

Example 3(b)

Alternative synthetic method of methyl (3R) 3-(tert-butyldimethylsilyloxy)-6-methylsulfinyl-5-oxohexanate (Ib-(R)-2)

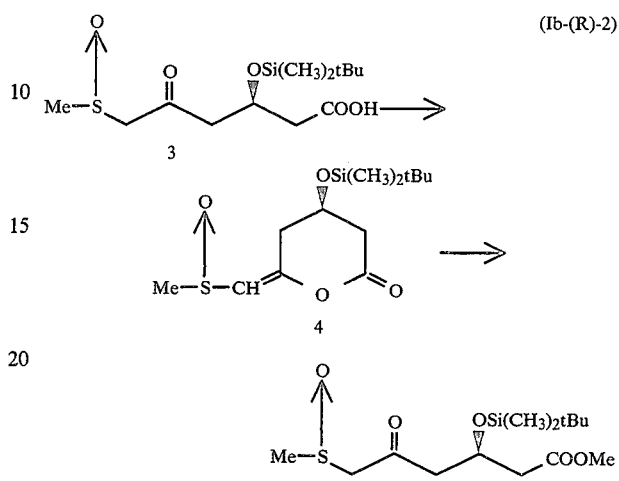

(1) To a solution of 348 mg (1.08 mM) of the compound 3 in 5 ml of methylene chloride are added 0.41 ml (2.7 eq) of triethylamine and 0.11 ml (1.3 eq) of methanesulfonyl chloride at −78° C. The mixture is stirred at room temperature for 2 hours and poured into diluted HCl, then extracted with methylene chloride to give 364 mg of the compound 4, which is found to be a mixture of four isomers by NMR analysis.

¹HNMR (CDCl₃): 0.09 (s, 6H); 0.86, 0.88 (2singlet, 9H); 2.68, 2.80 (2singlet, 3H); 2.60–2.90 (m, 4H); 4.2–4.4 (m, 1H); 5.54–5.59 (m, 1H)

(2) To a solution of 323 mg of the thus obtained compound 4 in 4 ml of methanol is added a methanol solution of 0.2 eq of sodium methoxide at 0° C., stirred for 20 minutes, poured into diluted HCl, then extracted with methylene chloride, dried, concentrated and subjected to column chromatography of silica gel for purification, to give 366 mg of the target compound (Ib-(R)-2) in a 82% yield.

The compounds obtained by the present inventions method are utilized for side chains of various HMG-CoA reductase inhibitors. One example thereof is shown below.

Reference Example

Synthesis of Sodium (+) 7-[4-(4-fluorophenyl)-2-isopropyl-5-methyl-(1-methylsulfonyl)pyrrol-3-yl]-(3R,5S)-dihydroxy-(E)-6-heptenate

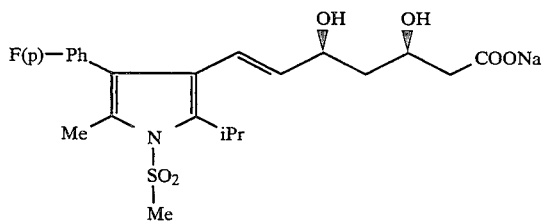

To a solution of 80 mg (0.15 mmol) of the compound (Ia-(R)-1) in 0.2 ml of acetonitrile, which is obtained in Example 1, is added 73 mg (0.225 mmol) of 4-(4-fluorophenyl)-3-formyl-2-isopropyl-5-methyl-1-methylsulfonylpyrrol under a nitrogen atmosphere at room temperature, and the mixture is refluxed for 11 hours and then removing the solvent to give methyl 7-[4-(4-fluorophenyl)-2-isopropyl-5-methyl-1-methylsulfonylpyrrol-3-yl]-3-(tert-butyldimethylsilyl)oxy-5-oxo-6-heptenate (Rf=0.45, ethyl acetate/toluene=1/6). To the obtained compound is added 1.5 ml of a solution of hydrogen fluoride in acetonitrile (i.e., 46% hydrogen fluoride solution diluted with acetonitrile to 20 times the original volume) at room temperature, then stirred for 1.5 hours, poured into an ice-cooled aqueous solution of sodium bicarbonate, and extracted twice with ethyl acetate. The organic layer is washed with brine, dried over anhydrous magnesium sulfate, and concentrated. The purification by column chromatography gives 43 mg of methyl 7-[4-(4-fluorophenyl)-2-isopropyl-5-methyl-1-methylsulfonylpyrrol-3-yl]-3-hydroxy-5-oxo-6-heptenate. (Rf=0.31, ethyl acetate/hexane=1/1).

To a solution of 67 mg (0.144 mmol) of the obtained compound in 1.2 ml of THF is added 0.3 ml of methanol, and 0.16 mmol of diethyl-methoxyborane in 160 μl of THF at −78° C. under nitrogen atmosphere, then stirred for 20 minutes. Next, 6 mg (0.16 mmol) of sodium borohydride is added thereto and stirred for 1.5 hours, then 0.2 ml of acetic acid is added thereto. The reaction mixture is poured into an ice-cooled aqueous solution of sodium bicarbonate and extracted with ethyl acetate twice. The organic layer is washed with brine, dried over anhydrous magnesium sulfate, and concentrated. To the resulting residue is added methanol, and concentrated again. This procedure is repeated three times, then the residue is purified by column chromatography to give 61 mg of a methyl ester (A) of the target compound with 91% yield (Rf=0.27, ethyl acetate/methylene chloride=1/3).

To a solution of 5.62 g (12.0 mmol) of the methyl ester compound (A) in 180 ml of ethanol is added dropwise 117 ml of 0.1N sodium hydroxide under ice-cooling, then stirred at room temperature for 1 hour. After removal of the solvent, 50 ml of ethanol is added, and is concentrated again. This procedure is repeated 3 times to give a residue, to which 100 ml of ether is added, then stirred at room temperature for 1 hour to give white crystals, which are collected by filtration, and washed with ether to give 5.47 g of the target compound with 96% yield.

Analysis ( % ) for C$_{22}$H$_{27}$NO$_6$SFNa.2H$_2$O: Calcd.: C,51.66; H,6.11; N,2.74; S,6.27; F,3.71; Na, 4.49 Found: C,51.79; H,6.17; N,2.84; S,6.12; F,3.49; Na,4.63 NMR (CDCl$_3$) δ: 1.33 (s, 3H); 1.37 (s, 3H); 2.15 (s, 3H); 2.24 (m, 2H); 3.36 (s, 3H); 3.72 (m, 2H); 4.21 (m, 1H); 4.98 (dd, J=16, 7 Hz, 1H); 6.62(d, J=16, 1H); 7.14 (m, 4H) [α]$_D$=+28.3±0.7° (C=1,010, 25.5° C., water)

Determination of optical purity

To a solution of 58 mg (0.124 mmol) of the methyl ester (A) in 0.6 ml of methanol, which is obtained in the above Reference Example, is added 62 μl of 4N-NaOH at 0° C., and stirred for 1 hour. After removal of the solvent, the residue is suspended in ethyl acetate and 0.15 ml of 2N-HCl is added thereto at 0° C, stirred at the same temperature for 5 minutes and dried over anhydrous magnesium sulfate. To the obtained solution is added an excess of diazoethane in ether at 0° C., and stirred for 5 minutes. After concentration, purification by column chromatography gives 49 mg of the following ethylester compound with a 82% yield.

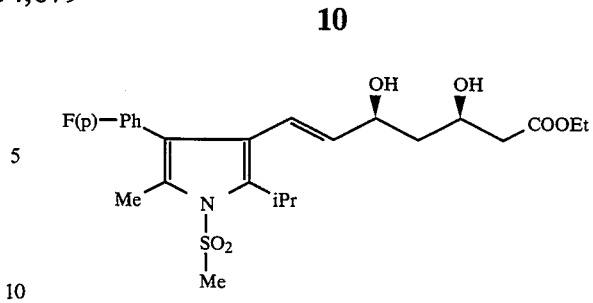

Rf: 0.25 (ethyl acetate/hexane=1/1)
High-performance liquid chromatography:
Column: Chiralcel (Daisel) OD 0.46×25 cm
Eluate: hexane/ethanol=90/10
Flow rate: 0.5 ml/min.
Wavelength: 254 nm
Temperature: 40° C.
Optical purity: 98% e e

Industrial Utility of The Invention

The present invention provides a synthetic method to produce optically active starting materials for various optically active medicaments, in more detail, HMG-CoA reductase inhibitors, in high optical purity and good yield.

We claim:
1. A method for synthesizing a compound (I):

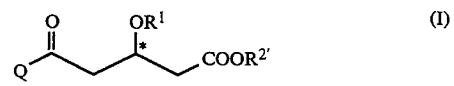

wherein
R$^1$ is hydrogen or a hydroxy protecting group;
R$^2$ is hydrogen, a lower alkyl or a substituted lower alkyl;
Q is —CH=P(R$^3$)$_3$ or —CHX'X
wherein
R$^3$ is a lower alkyl, a substituted lower alkyl, an aryl or a substituted aryl;
X is —P(O)R$^4$R$^5$ or —S(O)R$^4$
wherein
R$^4$ and R$^5$, each is hydrogen, a lower alkyl, a substituted lower alkyl, a lower alkoxy, a substituted lower alkoxy, an aryl, a substituted aryl, or halogen;
X' is hydrogen or lower alkyl;
*is an asymmetric carbon, which comprises
(a) subjecting glutarate (II):

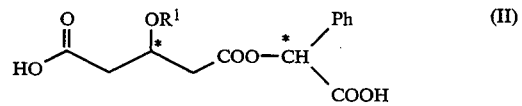

wherein R$^1$ and * are respectively the same as defined above, to a transesterification to produce a half-ester (III):

wherein R$^1$ is the same as defined above; R$^2$ is a lower alkyl or a substituted lower alkyl, then converting the free carboxylic acid to a reactive derivative, and reacting the derivative with a compound (IV a):

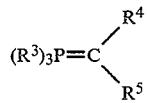

wherein $R^3$, $R^4$, and $R^5$ are respectively the same as defined above, or (b) reacting the compound (II) with $CH_2X'X$ (IV b) wherein X and X' are respectively the same as defined above.

2. The method according to claim 1, wherein the compound (II) is in a configuration of (3R, 2'R).

3. The method according claim 1, wherein the compound (II) is in a configuration of (3S, 2'S).

4. Methyl (3R)-3-(tert-butyldimethylsilyloxy)-5-oxo-6-triphenylphosphoranylidene hexanoate.

5. The method according to claim 1, further comprising the step of hydrolying the resulting product of step (a).

6. The method according to claim 1, further comprising the step of esterifying the resulting product of step (b).

UNITED STATES PATENT AND TRADEMARK OFFICE
CERTIFICATE OF CORRECTION

PATENT NO. : 5,354,879
DATED : October 11, 1994
INVENTOR(S) : T. Konoike, et al.

It is certified that error appears in the above-indentified patent and that said Letters Patent is hereby corrected as shown below:

In Column 2, top, correct the chemical structure II-(S) to show the proper steric configuration, thus:

In Column 2, line 50, rewrite "wherein $R^3$ $R^4$ and $R^5$" as: --wherein $R^3$, $R^4$ and $R^5$--.

In Column 4, about line 5, correct the chemical structure II-(S) to show the proper steric configuration, thus:

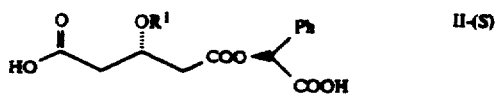

In Column 5, line 24, rewrite "C=1.04" as: --$C$=1.04--.

In Column 5, line 64, rewrite "C=1.27, 22.0° C." as: --$C$=1.27, 22.0° C.--.

In Column 6, in note 2 at about line 28, rewrite "(tertbutyldimethylsilyl)" as: --(tert-butyldimethylsilyl)--.

In Column 6, at about line 40, rewrite "2J$_{PH}$=22.6 Hz" as --$^2$J$_{PH}$=22.6 Hz--.

In Column 9, line 48, rewrite "$C_{22}H_{27}NO_6SFNa.2H_2O$" as: --$C_{22}H_{27}NO_6SFNa \cdot 2H_2O$--.

In Column 9, line 54, rewrite "C=1,010" as: --$C$=1.010--.

In Column 10, line 36, rewrite "$R^2$ is" as: --$R^{2'}$ is--.

In Column 10, line 50, rewrite "*is an asymmetric carbon" as: --"* is an asymmetric carbon"--.

UNITED STATES PATENT AND TRADEMARK OFFICE
CERTIFICATE OF CORRECTION

PATENT NO. : 5,354,879
DATED : October 11, 1994
INVENTOR(S) : T. Konoike, et al.

It is certified that error appears in the above-indentified patent and that said Letters Patent is hereby corrected as shown below:

In Column 12, claim 5, second line, rewrite "hydrolying" as --hydrolyzing--.

Signed and Sealed this

Twenty-seventh Day of February, 1996

Attest:

BRUCE LEHMAN

*Attesting Officer*      *Commissioner of Patents and Trademarks*